US005578721A

United States Patent [19]

Gupta et al.

[11] Patent Number: 5,578,721
[45] Date of Patent: Nov. 26, 1996

[54] PROCESS FOR PREPARATION OF 3-EXOMETHYLENE CEPHAM SULFOXIDE ESTERS

[75] Inventors: Niranjan L. Gupta; Ramanathan Sankaran, both of Bhopal; Shibu Varughese, Bangalose; Sakina Sitabkhan, Bhopal, all of India

[73] Assignee: Lupin Laboratories Limited, Maharashtra, India

[21] Appl. No.: 273,309

[22] Filed: Jul. 11, 1994

[51] Int. Cl.⁶ .................................................. C07D 501/02
[52] U.S. Cl. .................................................. 540/215
[58] Field of Search .................................. 540/222, 215

[56] References Cited

U.S. PATENT DOCUMENTS

| | | | |
|---|---|---|---|
| Re. 31,730 | 11/1984 | Bouzard | 544/30 |
| Re. 33,948 | 6/1992 | Schmidt | 514/194 |
| 3,641,014 | 2/1972 | Murphy | 260/243 |
| 3,665,003 | 5/1972 | Kennedy | 260/243 |
| 3,668,201 | 6/1972 | Gutowski | 260/243 |
| 3,668,202 | 6/1972 | Foster | 260/243 |
| 3,668,203 | 6/1972 | Clark | 260/243 |
| 3,716,533 | 2/1973 | Humber | 260/243 |
| 3,769,277 | 10/1973 | Long | 260/243 |
| 3,775,408 | 11/1973 | Ochiai | 260/243 |
| 3,792,995 | 2/1974 | Ochiai | 204/72 |
| 3,883,518 | 5/1975 | Ponticello | 260/243 |
| 3,917,587 | 11/1975 | Chauvette | 260/243 |
| 3,917,588 | 11/1975 | Chauvette | 260/243 |
| 3,925,372 | 12/1975 | Chauvette | 260/243 C |
| 3,932,392 | 1/1976 | Johnson | 260/243 |
| 3,932,393 | 1/1976 | Chauvette | 260/243 |
| 3,989,695 | 11/1976 | Scartazzini | 260/243 |
| 4,031,084 | 6/1977 | Kukolja | 260/243 |
| 4,048,162 | 9/1977 | Kukolja | 544/22 |
| 4,052,387 | 10/1977 | Kukolja | 544/22 |
| 4,060,688 | 11/1977 | Chauvette | 544/30 |
| 4,064,343 | 12/1977 | Chauvette | 544/16 |
| 4,068,071 | 1/1978 | Tsushima | 544/19 |
| 4,068,072 | 1/1978 | Tsushima | 544/19 |
| 4,075,203 | 2/1978 | Chou | 544/18 |
| 4,081,440 | 3/1978 | Kukolja | 260/239 |
| 4,113,940 | 9/1978 | Kamiya | 544/16 |
| 4,115,643 | 9/1978 | Kukolja | 544/16 |
| 4,123,612 | 10/1978 | Gorman | 544/16 |
| 4,147,864 | 4/1979 | Woodward | 544/16 |
| 4,159,272 | 6/1979 | Chou | 260/332 |
| 4,160,085 | 7/1979 | Tsuji | 544/16 |
| 4,160,091 | 7/1979 | Herron | 544/16 |
| 4,165,315 | 8/1979 | Kukolja | 260/239 |
| 4,165,316 | 8/1979 | Chou | 260/239 |
| 4,176,231 | 11/1979 | Corfield | 544/16 |
| 4,178,445 | 12/1979 | Takano | 544/30 |
| 4,182,870 | 1/1980 | Bruynes | 544/16 |
| 4,190,724 | 2/1980 | Chou | 544/16 |
| 4,208,515 | 6/1980 | Chauvette | 544/16 |
| 4,211,702 | 9/1980 | Hatfield | 260/239 |
| 4,223,133 | 9/1980 | Bunnell | 544/16 |
| 4,226,986 | 10/1980 | Hatfield | 544/16 |
| 4,230,620 | 10/1980 | Chou | 260/239.1 |
| 4,240,988 | 12/1980 | Bingham, Jr. | 260/989 |
| 4,252,950 | 2/1981 | Chauvette | 544/16 |
| 4,252,973 | 2/1981 | Slusarchyk | 544/21 |
| 4,254,029 | 3/1981 | Kaspi | 260/239 |
| 4,255,328 | 3/1981 | Woodward | 260/239 |
| 4,260,745 | 4/1981 | Chauvette | 544/16 |
| 4,271,305 | 6/1981 | Hatfield | 548/153 |
| 4,275,062 | 6/1981 | Breuer | 424/246 |
| 4,281,116 | 7/1981 | Chauvette | 544/16 |
| 4,281,117 | 7/1981 | Chauvette | 544/16 |
| 4,289,695 | 9/1981 | Chou | 260/239 |
| 4,301,278 | 11/1981 | Woodward | 544/16 |
| 4,301,279 | 11/1981 | Scartazzini | 544/16 |

(List continued on next page.)

*Primary Examiner*—John M. Ford
*Attorney, Agent, or Firm*—Ladas & Parry

[57] ABSTRACT

A process for the manufacture of 3-exomethylene cepham sulfoxide ester of the formula

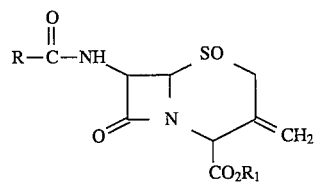

wherein R is hydrogen, $C_1$–$C_3$ alkyl, halomethyl, phenyl, substituted phenyl cyanomethyl, phenoxy, benzyloxy or substituted benzyl with a substituent group such as that selected from halo, alkyl, alkoxy, protected hydroxy, nitro, cyano and trifluoromethyl, a group of the formula $R_2$—O— wherein $R_2$ is t-butyl, 2,2,2-trichloro ethyl, benzyl or substituted benzyl; a group of the formula $R_3$—[O]$_n$—$CH_2$, wherein $R_3$ is phenyl or substituted phenyl with the substituent group selected from halo, alkyl, alkoxy, protected hydroxy, nitro, cyano, or 1,4-cyclohexadienyl, and n is 0 or 1; or a substituted arylalkyl group of formula $R_4$—CH where $R_4$ has the same meaning as $R_3$ defined above and W is a protected hydroxy or protected amino group; and $R_1$ is a carboxylic acid protecting group such as that selected from the group consisting of $C_1$–$C_4$ alkyl, 2,2,2-trihalo alkyl, benzyl, substituted benzyl such as para nitrobenzyl, phenacyl, halo substituted phenacyl and benzhydryl is disclosed. Such compound is prepared by reacting a chlorosulfinylazetidinone of the formula

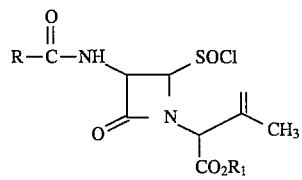

wherein R and $R_1$ have the same meanings as defined above, with a Lewis Acid type Friedel-Crafts catalyst and a sulfur compound in an inert solvent under anhydrous condition. These compounds find application as an intermediate for the preparation of cephalosporin antibiotics.

15 Claims, No Drawings

U.S. PATENT DOCUMENTS

| | | | |
|---|---|---|---|
| 4,301,280 | 11/1981 | Corfield | 544/16 |
| 4,304,718 | 12/1981 | Kamiya | 260/245 |
| 4,310,459 | 1/1982 | Cundall | 260/239.1 |
| 4,316,955 | 2/1982 | Abbott | 435/47 |
| 4,319,027 | 3/1982 | Woodward | 544/16 |
| 4,322,347 | 3/1982 | Cundall | 260/239.1 |
| 4,332,722 | 6/1982 | Tsuji | 260/245.4 |
| 4,334,063 | 6/1982 | Spry | 544/28 |
| 4,336,191 | 6/1982 | Kukolja | 260/239 |
| 4,338,436 | 7/1982 | Herron | 544/16 |
| 4,346,218 | 8/1982 | Tsuji | 544/16 |
| 4,354,022 | 10/1982 | Takaya | 544/28 |
| 4,363,807 | 12/1982 | Takaya | 544/16 |
| 4,366,315 | 12/1982 | Bruynes | 544/16 |
| 4,368,156 | 1/1983 | Spitzer | 260/239 |
| 4,368,325 | 1/1983 | Ueda | 544/16 |
| 4,374,982 | 2/1983 | Cundall | 544/16 |
| 4,385,176 | 5/1983 | Kamiya | 544/16 |
| 4,389,524 | 6/1983 | Scartazzini | 544/16 |
| 4,405,782 | 9/1983 | Palomo-Coll | 544/21 |
| 4,410,458 | 10/1983 | Kamiya | 260/239.1 |
| 4,431,803 | 2/1984 | Kukolja | 544/16 |
| 4,477,658 | 10/1984 | Scartazzini | 544/16 |
| 4,499,265 | 2/1985 | Torii | 544/16 |
| 4,513,134 | 4/1985 | Kim | 544/16 |
| 4,515,719 | 5/1985 | McShane | 260/239 |
| 4,518,773 | 5/1985 | Cundall | 544/16 |
| 4,558,123 | 12/1985 | McShane | 544/16 |
| 4,562,253 | 12/1985 | Prager | 544/19 |
| 4,591,642 | 5/1986 | Scartazzini | 544/16 |
| 4,623,645 | 11/1986 | Doherty | 514/200 |
| 4,629,542 | 12/1986 | Torii | 204/72 |
| 4,668,781 | 5/1987 | Scartazzini | 540/215 |
| 4,695,627 | 9/1987 | Verweij | 540/224 |
| 4,716,227 | 12/1987 | Furlenmeier | 540/230 |
| 4,767,851 | 8/1988 | Palomo-Coll | 540/218 |
| 4,853,468 | 8/1989 | Torii | 540/215 |
| 4,855,418 | 8/1989 | Cook | 540/205 |
| 4,888,100 | 12/1989 | Hertel | 204/157 |
| 4,921,954 | 5/1990 | Witkamp | 540/222 |
| 4,927,818 | 5/1990 | Takaya | 514/202 |
| 4,950,753 | 8/1990 | Copp | 540/230 |
| 4,958,018 | 9/1990 | Torii | 540/215 |
| 4,968,508 | 11/1990 | Oren | 424/468 |
| 4,985,554 | 1/1991 | Verweij | 540/215 |
| 4,994,454 | 2/1991 | Verweij | 540/215 |
| 5,015,725 | 5/1991 | Scoggins | 528/310 |
| 5,051,406 | 9/1991 | Satoh | 514/21 |
| 5,053,501 | 10/1991 | Kapur | 540/218 |
| 5,066,797 | 11/1991 | Baldwin | 540/215 |
| 5,070,195 | 12/1991 | Khanna | 540/218 |
| 5,095,107 | 3/1992 | Blanchard | 540/205 |
| 5,109,132 | 4/1992 | Verweij | 540/230 |
| 5,126,446 | 6/1992 | Brown | 540/230 |
| 5,132,419 | 7/1992 | Lanz | 540/215 |
| 5,142,043 | 8/1992 | Schreiber | 540/230 |
| 5,159,071 | 10/1992 | Khanna | 540/215 |
| 5,162,522 | 10/1992 | Naito | 540/230 |
| 5,204,458 | 4/1993 | Torii | 540/222 |
| 5,229,509 | 7/1993 | Nieves Elvira | 540/218 |
| 5,246,926 | 9/1993 | Bateson | 514/202 |
| 5,250,525 | 10/1993 | Kovacevic | 514/210 |
| 5,254,680 | 10/1993 | Alpegiani | 540/230 |
| 5,302,713 | 4/1994 | Yeh | 540/230 |
| 5,347,000 | 9/1994 | Khanna | 540/218 |
| 5,350,845 | 9/1994 | Brown, Jr. | 540/215 |

PROCESS FOR PREPARATION OF 3-EXOMETHYLENE CEPHAM SULFOXIDE ESTERS

The invention comprises a novel and improved process for the production of 3-Exomethylene cepham sulfoxide esters. More particularly, the present invention relates to an improved method for the preparation of 3-Exomethylene cepham sulfoxide ester by cyclisation of 2-chlorosulfinyl azetidin-4-one ester by an improved Lewis Acid type Friedel-Crafts catalyst.

The improved Lewis Acid type catalysts comprises a combination of Fe [III] or Sn [IV] or Ti [IV], Al or Zr [IV] chloride and a co-catalyst selected from organic divalent or tetravalent sulfur compound like dimethyl sulfide, carbon disulfide.

The starting material for the process of the present invention, namely, 2-chloro sulfinyl azetidin-4-one is normally prepared by reaction of a penicillin sulfoxide ester with an N-chloro halogenating agent.

3-Exomethylene cepham sulfoxide esters find important use as intermediates for the preparation of cephalosporin antibiotics. The most important of such anti-biotics is beta lactum anti-biotic such as Cefaclor.

The basic problem with the prior art processes were two-fold. The first one was with the preparation of the starting material itself and the second one was with respect to the preparation of the final sulfoxide ester.

Most prior art processes envisage synthesis of 3-Exomethylene cepham sulfoxide ester by conversion of penicillin sulfoxide ester to the corresponding 2-chloro sulfinyl azetidin-4-one followed by ring closure of the latter to the cepham sulfoxide ester. The reaction takes place in accordance with the scheme shown below:

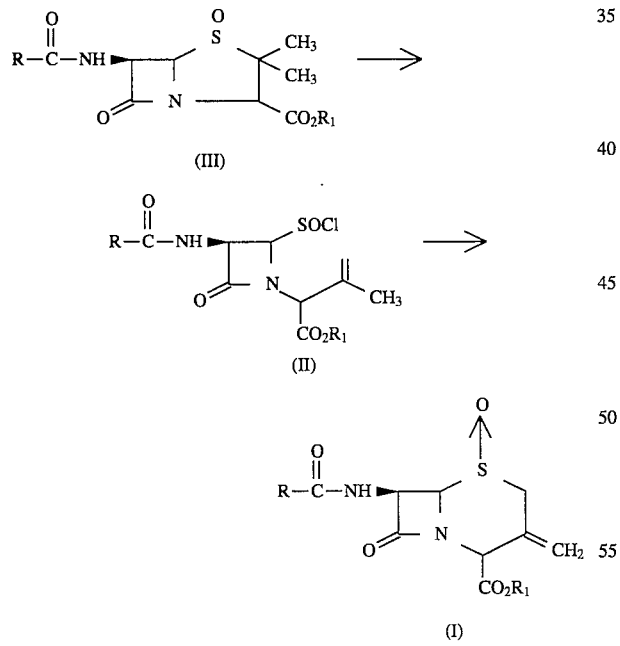

wherein R is:

hydrogen; $C_1$–$C_3$ alkyl; halomethyl; phenyl, substituted phenyl, cyanomethyl;

phenoxy, benzyloxy or substituted benzyl with the substituent group selected from halo, alkyl, alkoxy, protected hydroxy, nitro, cyano and trifluoromethyl;

a group of the formula $R_2$——O—— wherein $R_2$ is t-butyl, 2,2,2- trichloroethyl, benzyl or substituted benzyl;

a group of the formula $R_3$—(O)$_n$—$CH_2$ wherein $R_3$ is phenyl or substituted phenyl with the substituent group selected from halo, alkyl, alkoxy, protected hydroxy, nitro, cyano or 1,4-cyclohexadienyl, and n is 0 or 1; or a substituted arylalkyl group of formula

wherein $R_4$ has the same meaning as $R_3$ defined above and W is a protected hydroxy or protected amino group; and $R_1$ is a carboxylic acid protecting group selected from the group consisting of $C_1$–$C_4$ alkyl, 2,2,2-trihalo alkyl, benzyl, substituted benzyl, like p-nitrobenzyl, phenacyl, halo substituted phenacyl and benzyhydryl.

Prior U.S. Pat. Nos. 4,052,387 and 4,081,440 disclose processes for the preparation of 2-chloro sulfinyl azetidine-4-one by the treatment of the corresponding penicillin sulfoxide ester with an N-chloro halogenating agent in an inert solvent, the reaction being carried out in the presence (or absence) of an alkene oxide acid scavenger such as propylene oxide or butylene oxide to remove any hydrochloric acid formed during the reaction. Unfortunately, the subsequent conversion of 2-chloro sulfinyl azetidin-4-one to 3-chloro-cephem carboxylate is exceedingly poor being only in the range of 25% to 40%.

U.S. Pat. No. 4,165,315 discloses a method similar to that of the two above-mentioned U.S. patents.

U.S. Pat. Nos. 4,075,203 and 4,165,316 disclose the employment of a combination of alkylene oxide and calcium oxide as a hydrochloric acid scavenger in the reaction of a penicillin sulfoxide ester with an N-chloro halogenating agent to produce 2-chloro sulfinyl azetidin-4-one.

U.S. Pat. No. 4,289,695 discloses the use of a weakly basic, organic solvent-insoluble poly-4-vinyl pyridine polymer partially cross-linked with divinylbenzene as the hydrogen chloride acceptor in the ring-opening reaction for the conversion of a penicillin sulfoxide ester to 2-chloro sulfinyl azetidin-4-one. The product thus produced on reaction with a Lewis acid gives the corresponding 3-exomethylene cepham sulfoxide ester in a yield of from 10% to 76%. Unfortunately, poly-4-vinyl pyridine polymer is costly and for economic consideration, the hydrochloride produced therefrom requires regeneration to the original base for re-use which makes the entire operation extremely lengthy.

Finally, U.S. Pat. No. 5,070,195 discloses a similar process for the preparation of 2-chloro sulfinyl azetidin-4-one employing anion exchange resins as the acid trapping agent. These resins are shown to have the following structures:

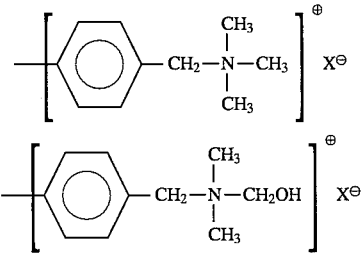

wherein X is a chloride, hydroxide or sulfate ion.

However, unless the hydrochloric acid generated during the reaction is simply adsorbed by the anion exchange resins, it is difficult to rationalise how such acid can be trapped by means of quaternary ammonium functionality since that would be equivalent to the reaction of quaternary ammonium chloride or sulphate with hydrochloric acid. It is, therefore, not surprising that poor yields of 2-chloro sulfinyl azetidin-4-one are obtained when anion exchange polymeric quaternary ammonium compounds are used as acid trapping agents according to U.S. Pat. No. 5,070,195.

The synthesis of the cepham sulfoxide esters of the formula I by cyclisation of 2-chlorosulfinyl azetidin-4-one ester has been disclosed in U.S. Pat. No. 5,126,446 dated Jun. 30, 1992, U.S. Pat. No. 4,190,724 dated Feb. 26, 1980 and U.S. Pat. No. 4,081,440 dated Mar. 28, 1978.

In all the patents disclosed above process comprises reacting penicillin sulfoxide esters [III] with the N-chlorohalogenating agent like N-chloro succinimide or N-chloro phthalimide in the presence of an acid [hydrochloric] scavanger like [a] alkylene oxide and calcium oxide or [b] partially cross-linked polyvinyl pyridine so as to produce 2-chloro sulfinyl azetidinone [II], followed by ring closure of [II] to produce [I] by means of a Lewis Acid such as stannic chloride, zirconium chloride or ferric chloride.

The U.S. Pat. No. 4,081,440 [Mar. 28, 1978] only describes the use of stannic chloride for conversion of compound [II] to [I].

On the other hand, U.S. Pat. No. 4,190,724 which is an improvement over U.S. Pat. No. 4,081,440 describes a complex of stannic chloride and an oxo compound selected from the group consisting of ethers; straight chain and cyclic ketones and phosphine oxides e.g. $R_1 R_2 R_3$ PO where R groups are alkyl or aryl for the conversion of [II] to [I].

U.S. Pat. No. 5,126,446 is an improvement for the production of compound [I] from [II]. This patent teaches complexation of the Lewis acid such as Stannic chloride or titanium chloride with nitro compound like nitromethane or nitroethane.

The conversion of [II] to [I] further improved when a combination of nitro compound, ether or ketone, and an olefin is used along with the Lewis acid.

The increase in yield of [I] from [II] in the above disclosed patents was reported to be between 2–4% over the control preparations. Such improvement in yield of [I] from [II] made the manufacture of the antibiotic more economical and useful.

However, the prior art has been silent as regards the catalyst i.e. Lewis acid and nitro or oxo compound. All that has been disclosed is a conjecture that the vacant orbital of the Lewis acid can accept a pair of electrons from the donor i.e. the ether, ketone or the nitro compound.

Further, it is difficult even to rationalise the structure when both the oxo compound and the nitro compound, or a mixture of oxo compound, nitro compound and an olefin is added to the Lewis Acid catalyst namely stannic chloride, zirconium chloride or titanium chloride.

The principal object of the present invention is the provision of a cost-effective, practically viable method for preparation in high yield of 3-Exomethylene cepham sulfoxide esters [I]. This is achieved by [1] ensuring that high yield of 2-chlorosulfinyl azetidin-4-one [II] is obtained in a cost-effective manner from the reaction of penicillin sulfoxide ester with an N-chlorohalogenating agent in which the undesirable deleterious acid generated is effectively removed from the reaction system without any interference in rates, course of the main reaction, and other deficiencies through a novel method and [ii] converting the resulting 2-chloro sulfinyl azetidin-4-one [II]into 3-exomethylene compound [I] in an improved and novel manner. The first step is achieved by the use of an inorganic, organic phosphates or acid phosphates or acid phosphates of an alkali metal, alkaline earth metal, ammonium, quaternary ammonium or mixtures thereof. Such intermediate process has been covered by applicants co-pending application No. 327/Bom/93 filed on Oct. 11, 1993.

The main object of the present invention is to effectively utilize the process covered in the co-pending application to obtain improved and higher yield of 3-exomethylene cepham sulfoxide esters [I] .

According to the process of this invention a chloro sulfinyl azetidin-one is reacted in an inert and dry solvent with a combination of Lewis Acid type Friedel-Crafts catalyst and a divalent or tetravalent organic sulfur compound under a specified range of temperature and time.

Accordingly, the present invention provides a process for the manufacture of 3-exomethylene cepham sulfoxide ester of the formula

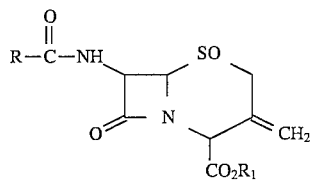

wherein R is hydrogen, $C_1$–$C_3$ alkyl, halomethyl, phenyl, substituted phenyl cyanomethyl, phenoxy, benzyloxy or substituted benzyl with a substituent group such as that selected from halo, alkyl, alkoxy, protected hydroxy, nitro, cyano and trifluoromethyl, a group of the formula $R_2$—O— wherein $R_2$ is t-butyl, 2,2,2-trichloro ethyl, benzyl or substituted benzyl;
a group of the formula $R_3$—[O]$_n$—$CH_2$, wherein $R_3$ is phenyl or substituted phenyl with the substituent group selected from halo, alkyl, alkoxy, protected hydroxy, nitro, cyano, or 1,4-cyclohexadienyl, and n is 0 or 1; or a substituted arylalkyl group of formula $R_4$-CH where $R_4$ has the same meaning as $R_3$
defined above and W is a protected hydroxy or protected amino group; and $R_1$ is a carboxylic acid protecting group such as that selected from the group consisting of $C_1$–$C_4$ alkyl, 2,2,2-trihalo alkyl, benzyl, substituted benzyl such as para nitrobenzyl, phenacyl, halo substituted phenacyl and benzhydryl which comprises reacting a chlorosulfinylazetidinone of the formula

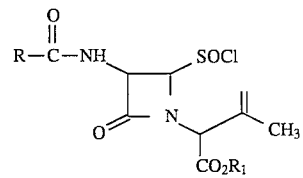

with a Lewis Acid type Friedel-Crafts catalyst and a sulfur compound in an inert solvent under anhydrous condition.

The Lewis Acid type Friedel-Crafts catalyst is selected from covalent chloride of Al, Sn[IV], Fe[III], Ti and Zirconium, e.g. $AlCl_3$, $FeCl_3$, $TiCl_4$, $ZrCl_4$.

The sulphur compound will be selected from dialkyl sulfide, carbocyclic sulfide diaryl sulfides, alkaryl sulfide, substituted diaryl sulfide substituent being halo, alkyl and aryl group being phenyl, naphthyl; alkyl being $C_1$ to long chain straight or branched alkyl, carbon disulfide, alkyl sulfoxides. Such sulfur compounds have the general structural features as
$R_5$-S-$R_6$, $R_6$-SO-$R_5$, $CS_2$, Ar-S-Ar, Ar-S-$R_5$, Ar-SO-Ar, Ar-SO-$R_5$, ArCH$_2$-S-CH$_2$-Ar, Ar-CH$_2$-SO-CH-hd 2, ArCH$_2$-S-$R_5$,

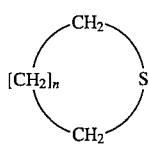

where n=2,3,4 and
where $R_5$ and $R_6$ are alkyl groups from $C_1$, $C_2$, $C_3$, $C_5$ to fatty alkyl groups such as methyl, ethyl propyl, isopropyl, butyl, sec butyl, pentyl and higher branched and straight chain alkyl group such as dodecyl, lauryl, cetyl; carbocyclic rings such as cyclo pentyl, cyclohexyl;
Ar is phenyl, naphthyl, alkyl substituted phenyl such as tosyl, halo substituted aryl such as chlorophenyl, bromophenyl, dichloro phenyl.

The 3-exo methylene cepham sulfoxide ester [I] is obtained in improved yields, generally to the range of between 12–22% by the process of the present invention compared to that obtained only with the stannic chloride catalyst alone. In other words, addition of aforesaid sulphur compounds to the Lewis acid catalyst like Sn[IV] chloride, Fe [III] chloride, Ti [IV] chloride, Zr [IV] chloride improves remarkably the efficiency of conversion of [II] to [I], thereby favorably affecting the economics of the process and subsequent cost of manufacture of the antibiotic viz Cefaclor.

In other words the aforesaid sulfur compounds act as a co-catalyst rendering the Lewis acid Friedel-Crafts catalyst more discriminating thereby improving the specificity of the desired reaction i.e. [I] from [II].

The process of the invention provides a 3-exo methylene cepham sulfoxide ester [I] by cyclising 2-chloro sulfinyl azetidin-4-one [II] with a Lewis acid Friedel-Crafts catalyst and a sulphur compound in an aprotic dry inert solvent under anhydrous conditions under specified range of time and temperature as shown below:

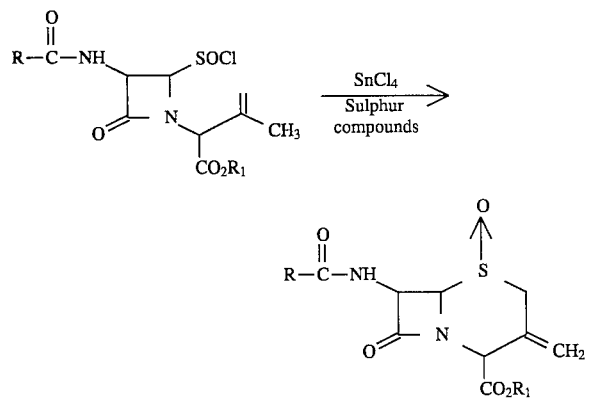

where R and $R_1$ are as described above.

In carrying out the process of this invention, the sulfur compound can be added to the solution of the sulfinyl chloride [II] before the addition of the catalyst or the catalyst complex of Lewis acid and the sulfur compound in an inert solvent can be added to II in a solution.

Inert organic solvents which can be employed in the cyclisation reaction of this invention are non-polar and preferably are the aromatic hydrocarbons such as benzene, toluene, xylene, chloroaromatics like chloro benzene, chloro toluene, tetralin, cyclohexane, cycloheptane, cyclopentane.

The catalyst complex formation is carried out at a temperature between −30° C. and 45° C. Preferably the catalyst complex is formed at a temperature between −10° C. and 25° C.

The molar ratio of 2-chloro sulfinyl azetindin-4-one, sulfur compound and the Lewis acid catalyst e.g. sn[IV] chloride, Ti[IV] chloride is maintained between 1:1–1.5: 2–3.

The time of the cyclisation reaction i.e. conversion of [II] to [I] through the use of Lewis acid catalyst-sulfur compound complex of this invention is between 12 hours to 30 hours, preferably being 16 hours to 24 hours.

The following examples further illustrate the process of this invention but is not to be construed as limitations thereof.

EXAMPLE 1

Preparation of p-Nitrobenzyl-7-Phenoxyacetamido-3-exomethylene-cepham-4-carboxylate-1-oxide.

Control experiment: Cyclisation without any sulfur compound

In a 3-liter 4 necked flask fitted with a mechanical stirrer, a thermowell and Dean Stark apparatus was added 50 g [0.353 moles] of anhydrous disodium hydrogen orthophosphate and 1.2 lit of toluene, and refluxed to remove moisture azeotropically. The reaction mixture was cooled to 30° C. and 50 gm, [0.099] moles of p-Nitrobenzyl-6-phenoxyacetamido-2,2-dimethylpenam-3-carboxylateol-1-oxide and 22 gm [0.121 moles] of N-chlorophthalimide was added and refluxed for 2 hour. The reaction mixture was cooled to 10° C., stirred for 30 min at 10° C. and filtered. After cooling the filtrate to −10° C., 51.9 gm [0.199] moles of stannic chloride in 50 ml toluene was added dropwise over a period of 40 min. at 0° C. and stirred for 16 hrs at 18° C. The complex thus formed was filtered, washed with hexane and added to methanol at 0° C. and stirred for 4 hr at 0° C. The slurry was filtered, washed with methanol and dried in vacuo to give 25 gm [50%] of the title compound m.p. 198° C.

EXAMPLE 2

Preparation of p-Nitrobenzyl-7-Phenoxyacetamido-3-exomethylene-cepham-4-carboxylate-1-oxide.

50 gm [0.353 moles] of anhydrous disodium hydrogen orthophosphate in 1.2 lit of toluene was taken in a 3 liter round bottom flask attached with a Dean Stark apparatus and refluxed to remove moisture azeotropically. The mixture was cooled and 50 gm [0.099 moles] of p-nitrobenzyl-6-phenoxyacetamido-2,2-dimethylpenam-3-carboxylate-1-oxide and 22 gm [0.121 moles] of N-chlorophthalimide were added and refluxed 120 min. The reaction mixture was cooled to 10° C. and stirred for 20 min. at 10° C. and filtered. After cooling the filtrate to −10° C, 12.4 gm [0.199 moles] of dimethyl sulfide was added followed by dropwise addition of 51.9 g [0.199 moles] of stannic chloride in 50 ml toluene at −10° C. The complex thus formed was stirred for 16 hr at 18° C. and filtered. The light brown coloured complex was washed with hexane and added to methanol at 25° C. and stirred for 4 hrs. The product was filtered, washed with methanol and dried in vacuum to give 35 gm [70%] of title product m.p. 192°–194° C.

IR cm$^{-1}$ [KBr]: 3400, 3000, 1780, 1695, 1600, 1520, 1350, 1240, 1190, 1120, 750, 690

$^1$H NMR: [CDCl$_3$]: Delta 3.61 [q,2H]; 4.52 [s,2H]; 4.93 [d,1H]; 5.35 [s,2H]; 5.38 [s,1H]; 5.51 [s,1H]; 5.79 [s,1H]; 6.12 [dd,1H]; 6.92–8.34 [m,9H].

Anal, calcd for $C_{23}$ $H_2$, $N_{3O8}$,S[499.5]

C: 55.31; H: 4.24; N.8.41%
Found C: 55.24; H: 4.30; N 8.39%

EXAMPLE 3

Preparation of
p-Nitrobenzyl-7-Phenoxyacetamido-3-exomethylene-cepham-4-carboxylate-1-oxide.

In a 3 liter round bottom flask fitted with a mechanical stirrer and a Dean Stark apparatus was added 45 gm [0.318 moles] of anhydrous disodium hydrogen orthophosphate and 1.2 lit of toluene and refluxed to remove moisture. After cooling the suspension, 50 gm [0.0990 moles] of p-Nitrobenzyl-6-phenoxyacetamido-2,2-dimethylpenam-3-carboxylate-1-oxide and 22 gm [0.121 moles] of N-chlorophthalimide were added and mixture refluxed for 120 min. The mixture was cooled to 10° C., filtered and after cooling to −10° C. was added 12.4 gm [0.199 moles] of dimethyl sulfide, 15.23 gm [0.2495 moles] of nitromethane followed by dropwise addition of 51.9 gm [0.199 moles] of stannic chloride in 10 ml of toluene at −10° C. The resulting complex was stirred for 16 hr at +18° C. The complex was filtered washed with hexane and added to methanol at 0° C. and stirred for 4 hr at 10° C. The slurry was filtered and the product washed with methanol, dried under vacuum at 40° C. to give 36.5 gm [73%] of title product.

EXAMPLE 4

Preparation of
p-Nitrobenzyl-7-Phenoxyacetamido-3-exomethylene-cepham-4-carboxylate-1-oxide.

4.5 gm [0.0318 moles] of anhydrous disodium hydrogen orthophosphate in 300 ml of toluene was binary distilled to remove moisture using Dean Stark trap. After cooling the suspension to 30° C., 5 gm [9.98 m moles] of p-Nitrobenzyl-6-phenoxyacetamido-2,-dimethylpenam-3-carboxylate-1-oxide and 2.2 gm [12.12 m moles] of N-chlorophthalimide were added and refluxed for 120 min. The mixture was cooled to 10° C., stirred for 30 min. and filtered. After cooling to −10° C., 0.759 gm [9.98 m moles] of carbon disulfide was added followed by dropwise addition of 5 gm [19.19 m moles] of stannic chloride in 5 ml toluene and stirred for 16 hr at 18° C. The complex was filtered, washed with hexane and added to methanol at 0° C. After stirring the slurry for 4 hrs, the product was filtered, washed with methanol, dried under vacuum at 40° C. to give 3.4 gm [68%] of title product.
IR[KBr, cm$^{-1}$]: 3400, 3000, 1780, 1600, 1520, 1350, 1240, 1190, 1120, 750, 690
$^1$HNMR: [CDCl$_3$]: Delta 3.61 [q,2H]; 4.52 [s,2H]; 4.93 [d,1H]; 5.35 [s,2H]; 5.51 [s,1H]; 5.79 [s,1H], 6.12 [dd,1H]; 6.92–8.34 [m,9H].

EXAMPLE 5

Preparation of
p-Nitrobenzyl-7-Phenoxyacetamido-3-exomethylene-cepham-4-carboxylate-1-oxide.

1.8 gm [0.0127 moles] of anhydrous disodium hydrogen orthophosphate, 150 ml of dry toluene, 2g [3.99 m moles] of p-nitrobenzyl-6-phenoxyacetamido-2,2-dimethylpenam-3-carboxylate-1-oxide and 0.869 gm [4.79 m moles] of N-chlorophthalimide were added and refluxed for 120 min. The mixture was cooled to 10° C., stirred for 30 min. and filtered. After cooling the filtrate to −10° C., 0.407 gm [3.99 m moles] of pentamethylene sulfide was added followed by dropwise addition of 2.07 gm [0.0079 moles] of stannic chloride in 2 ml toluene and stirred for 16 hr at +18° C. The complex was filtered, washed with hexane and added to methanol at 0° C. After stirring the slurry for 4 hrs, the product was filtered, washed with methanol, dried under vacuum at 40° C. to give 1.35 gm of title product [67.5%] m.p. 194° C.

EXAMPLE 6

Preparation of
p-Nitrobenzyl-7-Phenoxyacetamido-3-exomethylene-cepham-4-carboxylate-1-oxide.

1.8 gm [0.0127 moles] of anhydrous disodium hydrogen orthophosphate, 150 ml of dry toluene, 2 gm [3.99 m moles] of p-nitrobenzyl-6-phenoxyacetamido-2,2-dimethylpenam-3-carboxylate-1-oxide and 0.869 gm [4.79 m moles] of N-chlorophthalimide were added and refluxed for 120 min. The mixture was cooled to 10° C., stirred for 30 min. and filtered. After cooling the filtrate to −10° C., 0.407 gm [3.99 m moles] of pentamethylene sulfide was added followed by dropwise addition of 2.07 gm [0.0079 moles] of stannic chloride in 2 ml toluene and stirred for 16 hr at +18° C. The complex was filtered, washed with hexane and added to methanol at 0° C. and stirred for 4 hrs at 0° C. The off-white product was filtered, washed with methanol, dried under vacuum at 40° C. to give 1.38 gm of the title product [69%].

EXAMPLE 7

Preparation of
p-Nitrobenzyl-7-Phenoxyacetamido-3-exomethylene-cepham-4-carboxylate-1-oxide.

1.8 gm [0.0127 moles] of anhydrous disodium hydrogen orthophosphate, 2 gm [3.99 m moles] of p-Nitrobenzyl-6-phenoxyacetamido-2,2-dimethylpenam-3-carboxylate-1-oxide and 0.869 gm [4.79 m moles] of N-chlorophthalimide in 150 ml of dry toluene were refluxed for 120 min. The yellow coloured suspension was cooled to 10° C. and filtered to remove insoluble solids. After cooling the filtrate to −10° C., 0.855 gm [3.99 m moles] of benzyl sulfide and 2.07 gm [7.98 m moles] of stannic chloride in 2 ml of toluene was added and stirred for 16 hr. at 18° C. The complex was filtered, washed with hexane and added to methanol at 0° C. The off-white product was filtered, washed with methanol, dried under vacuum at 40° C. to give 1.34 gm [67%] of the title product.

EXAMPLE 8

Preparation of
p-Nitrobenzyl-7-Phenoxyacetamido-3-exomethylene-cepham-4-carboxylate-1-oxide.

1.8 gm [0.0127 moles] of anhydrous disodium hydrogen orthophosphate, 2 gm [3.99 m moles] of p-Nitrobenzyl-6-phenoxyacetamido-2,2-dimethylpenam-3-carboxylate-1-oxide and 0.869 gm [4.79 m moles] of N-chlorophthalimide in 150 ml of dry toluene were refluxed for 120 min. The yellow coloured suspension was cooled to 10° C., stirred for 30 min. and filtered to remove insoluble solids. After cooling the filtrate to −10° C., 0.743 gm [3.99 m moles] of phenyl sulfide and 2.07 gm [7.98 m moles] of stannic chloride in 2 ml of toluene was added and stirred for 16 hrs. at 18° C. The complex was filtered, washed with hexane and added to methanol at 0° C. The off-white product was filtered, washed with methanol, dried under vacuum at 40° C. to give 1.24 gm [62%] of the title product.

EXAMPLE 9

Preparation of
p-Nitrobenzyl-7-Phenoxyacetamido-3-exomethylene-cepham-4-carboxylate-1-oxide.

9.0 gm [0.0636 moles] of anhydrous disodium hydrogen orthophosphate, 10 gm [0.0 199 m moles] of p-Nitrobenzyl-6-phenoxyacetamido-2,2-dimethylpenam-3-carboxylate-1-oxide and 4.4 gm [24.20 m moles] of N-chlorophthalimide in 600 ml of dry toluene was refluxed for 120 min. The yellow coloured suspension was cooled to 10° C., stirred for 30 min. and filtered to remove insoluble solids. After cooling the filtrate to –10° C., 1.247 gm [0.20 moles] of dimethyl sulfide and 11.6 gm [0.0499 moles] of zirconium tetrachloride were added with the aid of 10 ml of toluene at –10° C. and stirred for 24 hrs. at 18° C. and filtered. The light brown coloured complex was washed with hexane and added to methanol at 25° C. and stirred for 4 hrs. The product was filtered, washed with methanol and dried in vacuum to give 6.4 gm [64%] of the title product.
$^1$HNMR: [CDCl$_3$] Delta 3.61 [q,2H]; 4.52 [s,2H]; 4.93 [d,1H]; 5.35 [s,2H]; 5.38 [s,1H]; 5.5 1 [s,1H], 5.79 [s,1H]; 6.12 [dd,1H]; 6.92–8.34 [m, 1H].

EXAMPLE 10

Preparation of
p-Nitrobenzyl-7-Phenoxyacetamido-3-exomethylene-cepham-4-carboxylate-1-oxide.

4.5 gm [0.032 moles] of anhydrous disodium hydrogen orthophosphate in 300 ml toluene was refluxed azeotropically to remove moisture using Dean Stark apparatus. The suspension was cooled to 30° C., 5 gm [0.0099 moles] of p-Nitrobenzyl-6-phenoxyacetamido-2,-dimethylpenam-3-carboxylate-1-oxide and 2.2 gm [0.012 moles] of N-chlorophthalimide were added and refluxed for 120 min. The filtrate was cooled to –10° C., and to this was added 0.62 gm [9.9 m moles] of dimethyl sulfide, 1.52 gm [0.025 moles] of nitromethane and 5.8 g [0.0248 moles] of zirconium chloride with the aid of 5 ml toluene. The complex was washed with hexane and added to methanol at 0° C. The slurry was stirred for 4 hrs. at 0° C. and filtered. The product dried under vacuum weighed 3.4 gm [68%] of the title product.

EXAMPLE 11

Preparation of
p-Nitrobenzyl-7-Phenoxyacetamido-3-exomethylene-cepham-4-carboxylate-1-oxide.

In a 500 ml four necked round bottom flask fitted with a mechanical stirrer and a Dean Stark apparatus was added 4.5 gm [0.032 moles] of anhydrous disodium hydrogen orthophosphate, 300 ml of dry toluene, 5 gm [9.98 m moles] of p-Nitrobenzyl-6-phenoxyacetamido-2,2-dimethylpenam-3-carboxylate-1-oxide and 2.2 gm [12.12 m moles] of N-chlorophthalimide and refluxed for 2 hr. The suspension was cooled to 10° C., filtered and after cooling the filtrate to –10° C., was added 0.753 g [9.98 m moles] of carbon disulfide followed by 5.8 gm [24.8 m moles] of zirconium chloride and stirred for 24 hrs at 25° C. The complex slurry was filtered, washed with hexane and added to Methanol at 0° C. The product was filtered washed and dried to give 3.25 gm of title product [65%].

EXAMPLE 12

Preparation of
p-Nitrobenzyl-7-Phenoxyacetamido-3-exomethylene-cepham-4-carboxylate-1-oxide.

In a 250 ml four necked round bottom flask fitted with a Dean Stark apparatus was added 1.8 gm [0.0 126 moles] of anhydrous disodium hydrogen orthophosphate, 2 gm [3.99 m moles] of p-Nitrobenzyl-6-phenoxyacetamido-2,2-dimethylpenam-3-carboxy-late-1-oxide and 0.869 gm of [4.79 m moles] of N-chlorophthalimide in 150 ml of dry toluene and refluxed for 120 min. The yellow coloured suspension was cooled to 10° C., stirred for 30 min. and filtered to remove insoluble solids. After cooling the filtrate to –10° C., 0.743 gm [3.99 m moles] of phenyl sulfide and 1.86 gm [7.98 m moles] of zirconium chloride were added and stirred for 24 hr. at 18° C. The complex slurry was filtered, washed with hexane and added to Methanol at 0° C. The product was filtered washed and dried to give 1.2 gm of title product [60%].

EXAMPLE 13

Preparation of
p-Nitrobenzyl-7-Phenoxyacetamido-3-exomethylene-cepham-4-carboxylate-1-oxide.

In a 250 ml four necked round bottom flask fitted with a mechanical stirrer and a Dean Stark apparatus was added 1.8 gm [0.0126 moles] of anhydrous disodium hydrogen orthophosphate, 2 gm [3.98 m moles] of p-Nitrobenzyl-6-phenoxyacetamido-2,2-dimethylpenam-3-carboxylate-1-oxide and 0.869 gm [4.79 m moles] of N-chlorophthalimide in 150 ml of dry toluene and refluxed for 120 min. and filtered to remove insoluble solids. After cooling the filtrate to –10° C., 0.855 gm [3.99 m moles] of benzyl sulfide and 1.86 gm [7.98 m moles] of zirconium chloride were added and stirred for 24 hr. at 18° C. The complex slurry was filtered, washed with hexane and added to Methanol at 0° C. The product was filtered washed and dried to give 1.2 gm of title product [60%].

EXAMPLE 14

Preparation of
p-Nitrobenzyl-7-Phenoxyacetamido-3-exomethylene-cepham-4-carboxylate-1-oxide.

In a 250 ml four necked round bottom flask fitted with a mechanical stirrer and a Dean Stark apparatus was added 1.8 gm [0.0126 moles] of anhydrous disodium hydrogen orthophosphate, 2 gm [3.98 m moles] of p-Nitrobenzyl-6-phenoxyacetamido-2,2-dimethylpenam-3-carboxylate-1-oxide and 0.869 gm [4.79 m moles] of N-chlorophthalimide in 150 ml of dry toluene and refluxed for 120 min. The yellow coloured suspension was cooled to 10° C., stirred for 30 min. and filtered to remove insoluble solids. After cooling the filtrate to –10° C., dimethyl sulfoxide 0.311 gm [3.98 m moles] was added followed by the addition 1.86 g [7.98 m moles] of zirconium chloride were added and stirred for 24 hr. at +18° C. The complex slurry was filtered, washed with hexane and added to Methanol at 0° C. The product was filtered washed and dried to give 1.3 gm of title product [65%].

EXAMPLE 15

Preparation of p-Nitrobenzyl-7-Phenoxyacetamido-3-exomethylene-cepham-4-carboxylate-1-oxide.

In a 250 ml four necked flask fitted with a mechanical stirrer and a Dean Stark apparatus was added 1.8 gm [0.0126 moles] of anhydrous disodium hydrogen orthophosphate, 2 gm [3.98 m moles] of p-Nitrobenzyl-6-phenoxyacetamido-2,2-dimethylpenam-3-carboxylate-1-oxide and 0.869 gm [4.79 m moles] of N-chlorophthalimide in 150 ml of dry toluene and refluxed for 120 min. The yellow coloured suspension was cooled to 10° C. stirred for 30 min. and filtered to remove insoluble solids. After cooling the filtrate to −10° C., 0.407 gm [3.99 m moles] of pentamethylene sulfide followed by addition of 1.86 gm [7.98 m moles] of zirconium chloride and stirred for 24 hr. at 18° C. The complex slurry was filtered, washed with hexane and added to Methanol at 0° C. The product was filtered washed with methanol and dried to give 1.24 gm of title product [62%].

EXAMPLE 16

Preparation of p-Nitrobenzyl-7-Phenoxyacetamido-3-exomethylene-cepham-4-carboxylate-1-oxide.

In a one liter four necked flask fitted with a mechanical stirrer and a Dean Stark apparatus was added 9.0 gm [0.063 moles] of anhydrous disodium hydrogen orthophosphate, 10 gm [0.0199 m moles] of p-Nitrobenzyl-6-phenoxyacetamido-2,2-dimethylpenam-3-carboxylate-1-oxide and 4.16 gm [0.0229 m moles] of N-chlorophthalimide in 600 ml of dry toluene and refluxed for 120 min. The yellow coloured suspension was cooled to 10° C., stirred for 30 min. and filtered to remove insoluble solids. After cooling the filtrate to −10° C., 1.247 gm [0.02 m moles] of dimethyl sulfide and 7.56 gm [0.0399 m moles] of titanium chloride was added and stirred for 24 hours at 18° C. The complex slurry was washed with hexane and added to methanol at 0° C. and stirred for 4 hrs. at 0° C. The product was filtered, washed with methanol and dried to give 6.8 gm of title product [68%].

EXAMPLE 17

Preparation of p-Nitrobenzyl-7-Phenoxyacetamido-3-exomethylene-cepham-4-carboxylate-1-oxide.

1.8 gm [0.0127 moles] of disodium hydrogen orthophosphate, 2 gm [3.98 m moles] of p-Nitrobenzyl-6-phenoxyacetamido-2,2-dimethylpenam-3-carboxylate-1-oxide and 0.869 gm [4.79 m moles] of N-chlorophthalimide in 150 ml of dry toluene was refluxed for 100 min. The suspension was cooled to 10° C. and filtered. After cooling the filtrate to −10° C., 0.753 gm [9.98 m moles] of carbon disulfide was added followed by 1.514 gm [7.98 m moles] of titanium chloride and the resultant complex was stirred for 24 hrs at +18° C. and filtered. The complex was washed with hexane, and added to Methanol at 0° C. After stirring the slurry for 4 hrs. the product was filtered, washed with methanol and dried under vacuum to give 1.28 gm [64%] of title product.

EXAMPLE 18

Preparation of p-Nitrobenzyl-7-Phenoxyacetamido-3-exomethylene-cephamo-4-carboxylate-1-oxide.

1.8 gm [0.0127 moles] of anhydrous disodium hydrogen orthophosphate and 2 gm [3.98 m moles] of p-Nitrobenzyl-6-phenoxyacetamido-2,2-dimethylpenam-3-carboxylate-1-oxide 0.869 gm [4.79 m moles] of N-chlorophthalimide in 150 ml of dry toluene was refluxed for 100 min. The suspension was cooled to 10° C. and filtered. After cooling the filtrate to −10° C., 0.407 gm [3.98 m moles] of pentamethylene sulfide was added followed by 1.514 gm [7.98 m moles] of titanium chloride and the resultant complex was stirred for 24 hrs. at 18° C. and filtered. The complex was washed with hexane and added to methanol at 0° C. After stirring the slurry for 4 hrs. the product was filtered, washed with methanol and dried under vacuum to give 1.2 gm [60%] of the product m.p. 194° C.

EXAMPLE 19

Preparation of p-Nitrobenzyl-7-Phenoxyacetamido-3-exomethylene-cepham-4-carboxylate-1-oxide.

1.8 gm [0.0127 moles] of anhydrous disodium hydrogen orthophosphate and 2 gm [3.98 m moles] of p-Nitrobenzyl-6-phenoxyacetamido-2,2-dimethylpenam-3-carboxylate-1-oxide 0.869 gm [4.79 m moles] of N-chlorophthalimide in 150 ml of dry toluene was refluxed for 100 min. The suspension was cooled to 10° C. and filtered. After cooling the filtrate to −10° C., 0.855 gm [3.99 m moles] of benzyl sulfide followed by 1.514 gm [7.98 m moles] of titanium chloride were added and the resultant complex was stirred for 24 hrs. and filtered. The complex was washed with hexane and added to methanol at 0° C. and filtered, washed with methanol and dried under vacuum to give 1.24 gm of the title product [62%].

EXAMPLE 20

Preparation of p-Nitrobenzyl-7-Phenoxyacetamido-3-exomethylene-cepham-4-carboxylate-1-oxide.

In a 250 ml 4 necked round bottom flask fitted with a Dean Stark apparatus, 1.8 gm [0.0127 moles] of anhydrous disodium hydrogen orthophosphate, 2 gm [3.99 m moles] of p-Nitrobenzyl-6-phenoxyacetamido-2,2-dimethylpenam-3-carboxylate-1-oxide 0.869 gm [4.78 m moles] of N-chlorophthalimide in 150 ml of dry toluene was refluxed for 120 min. The suspension was cooled to 10° C. and filtered. After cooling to −10° C., 0.743 gm [3.99 m moles] of phenyl sulfide and 1.514 gm [7.98 m moles] of titanium chloride were added and the resultant complex was stirred for 24 hrs. and filtered. The complex was washed with hexane and added to methanol at 0° C. and the resultant slurry stirred for 4 hrs. at 0° C. The product was filtered, washed with methanol and dried under vacuum to give 1.24 gm of the title product [62%].

EXAMPLE 21

Preparation of p-Nitrobenzyl-7-Phenoxyacetamido-3-exomethylene-cepham-4-carboxylate-1-oxide.

In a 250 ml 4 necked round bottom flask fitted with a Dean Stark apparatus, 1.8 gm [0.0127 moles] of anhydrous disodium hydrogen orthophosphate, 2 gm [3.99 m moles] of p-Nitrobenzyl-6-phenoxyacetamido-2,2-dimethylpenam-3-carboxylate-1-oxide 0.869 gm [4.78 m moles] of N-chlorophthalimide in 150 ml of dry toluene was refluxed for 120 min. The suspension was cooled to 10° C. and filtered. After cooling to −10° C., 0.311 gm [3.99 m moles] of dimethyl sulfoxide followed by 1.514 gm [7.98 m moles] of titanium chloride were added and the resultant complex was stirred for 24 hrs. and filtered. The complex was washed with hexane and added to methanol at 0° C. and the resultant slurry stirred for 4 hrs. at 0° C. The product was filtered, washed with methanol and dried under vacuum to give 1.32 gm of title product [66%].

EXAMPLE 22

Preparation of p-Nitrobenzyl-7-Phenoxyacetamido-3-exomethylene-cepham-4-carboxylate-1-oxide.

950 ml of toluene was taken in a 4 necked 2 lit round bottom flask. To this was added 14.5 gm [0.102 moles] of anhydrous disodium hydrogen orthophosphate and mixture refluxed to remove moisture using Dean Stark trap. The suspension was cooled to 30° C. and 10 gm [0.0206 moles] of p-nitrobenzyl-6-phenylacetamido-2,2-dimethylpenam-3-carboxylate-1-oxide and 5.49 gm [0.0302 moles] of N-chlorophthalimide were added and refluxed for 100 min. The contents were cooled to 10° C., filtered and after cooling the filtrate to −30° C., 1.0 gm [0.0162 moles] of dimethyl sulfide was added followed by dropwise addition of 9.65 gm [0.0370 moles] of stannic chloride in 5 ml toluene at −30° C., and stirred for 16 hr at 15° C. The complex was filtered, washed with hexane and added to methanol at 0° C. The slurry was stirred for 4 hrs. and filtered to give 7.0 gm [70%] of the title product m.p. 203° C.

'HNMR: [CDCl$_3$]: Delta 3.30–3.80 [m,4H]; 5.30 [d,1H]; 5.25 [s,3H]; 5.45 [s,1H]; 5.75 [s,1H]; 6.00 [dd,1H]; 6.90 [d,1H] and 7.20–8.40 [m,9H].

EXAMPLE 23

Preparation of p-Nitrobenzyl-7-Phenoxyacetamido-3-exomethylene-cepham-4-carboxylate-1-oxide.

12.5 gm [0.088 moles] of anhydrous disodium hydrogen orthophosphate in 300 ml toluene was refluxed using Dean Stark apparatus to remove moisture azeotropically. The suspension was cooled to 60° C. and 10 gm [0.0201 moles] of 2,2,2-trichloroethyl-6-phenoxyacetamido-2,2-dimethylpenam-3-carboxylate-1-oxide and 5.38 gm [0.0296 moles] of N-chlorophthalimide was added and refluxed for 160 min. The mixture was cooled to 10° C., stirred for 30 min. at 10° C. and filtered. The filtrate was cooled to 0° C. and 1.248 gm [0.0201 moles] of dimethyl sulfide was added followed by dropwise addition of 9 gm [0.0345 moles] of stannic chloride in 10 ml toluene at 0° C. After complete addition, the mixture was stirred for 16 hr. at room temperature. The complex was filtered, washed with hexane and added to methanol at 10° C. and the resultant slurry was stirred for 4 hors. at 10° C. The slurry was filtered, washed with methanol, dried under vacuum at 40° C. to give 7.2 gm of title product [72%].

'HNMR: [CDCl$_3$]: Ù3.70 [q,2H C2H]; 4.54 [s,2H] C$_6$H$_5$OCH$_2$; 4.81 [AB$_q$2H], [OCH$_2$ CCl$_3$]; 4.95 [d,1H]; 5.37, 5.82 [2s,2H,CH$_2$]; 5.51 [s,1H,C$_4$H]; 6.06 [dd,1H, C$_7$H]; 6.80–7.30 [m,5H Ar]; 8.25 [d,1H,NH].

EXAMPLE 24

Preparation of p-Nitrobenzyl-7-Phenoxyacetamido-3-exomethylene-cepham-4-carboxylate-1-oxide.

12.5 gm [0.088 moles] of anhydrous disodium hydrogen orthophosphate in 500 ml toluene was refluxed using Dean Stark trap to remove moisture azeotropically. The suspension was cooled and 10 gm [0.0201 moles] of 2,2,2-trichloroethyl-6-phenoxyacetamido-2,2-dimethylpenam-3-carboxy-late-1-oxide and 5.40 gm [0.0297 moles] of N-chlorophthalimide was added and refluxed for 160 min. The reaction mixture was cooled to 0° C. and 1.489 gm [0.0195 moles] of carbon disulphide was added followed by dropwise addition of 9.42 gm [0.0362 moles] of stannic chloride in 10 ml toluene at 0° C. The complex slurry was stirred for 36 hrs. at room temperature and filtered. The organce complex was washed with hexane and added to methanol at 10° C. The slurry was stirred for 4 hors. at 10° C. and filtered. The product was washed with methanol and dried in vacuum at 40° C. to give 7.4 gm [74%] of title product.

EXAMPLE 25

Preparation of p-Nitrobenzyl-7-Phenoxyacetamido-3-exomethylene-cepham-4-carboxylate-1-oxide.

9 gm [0.516 moles] of anhydrous dipotassium hydrogen orthophosphate in 600 ml toluene was refluxed azeotropically to remove moisture. After cooling the suspension to 30° C., add 10 gm [0.0199 moles] of p-nitrobenzyl-7-phenoxyacetamido-2,2-dimethylpenam-3-carboxylate-1-oxide and 4.2 gm [0.023 moles] of N-chlorophthalimide and reflux for 120 min. Cool the suspension to 10° C. and stir for 30 min. at 10° C. Filter the reaction mixture and cool the filtrate to −10° C. and add 1.24 gm [0.0199 moles] of dimethylsulfide followed by dropwise addition of 10.36 gm [0.0398 moles] of stannic chloride in 10 ml toluene at −10° C. and stir the resultant complex slurry for 16 hrs. at 18° C. The complex was filtered, washed with hexane and added to methanol at 0° C. The product slurry was stirred for 4 hrs. at 0° C. and filtered, washed with methanol, dried under vacuum to give 7.0 gm [70%]of title product m.p. 198° C.

EXAMPLE 26

Preparation of p-Nitrobenzyl-7-Phenoxyacetamido-3-exomethylene-cepham-4-carboxylate-1-oxide.

6.3 gm [0.036 moles] of anhydrous dipotassium hydrogen orthophosphate in 430 ml toluene was binary distilled to remove moisture. To the cooled suspension was added 7 gm [0.0 139 moles] of p-nitrobenzyl-7-phenoxyacetamido-2,2-dimethylpenam-3-carboxylate-1-oxide and 2.94 gm [0.0162 moles] of N-chlorophthalimide and reflux for 120 min. Cool the suspension to 10° C. and filter. Cool the filtrate to −10° and add 1.06 g [0.0139 moles] of carbon disulfide followed by dropwise addition of 7.25 gm [0.0278 moles] of stannic chloride in 7.0 ml toluene at 0° C. and stir the resultant complex slurry for 16 hrs. at +18° C. The complex was filtered, washed with hexane and added to methanol at 0° C. The product slurry was stirred for 4 hrs. at 0° C. and filtered, washed with methanol, dried under vacuum to give 4.76 gm [68%] of title product m.p. 195° C.

EXAMPLE 27

Preparation of
p-Nitrobenzyl-7-Phenoxyacetamido-3-exomethylene-cepham-4-carboxylate-1-oxide.

8 gm [0.0587 moles] of anhydrous dicalcium hydrogen phosphate in 600 ml toluene was binary distilled to remove moisture. After cooling the suspension to 30° C. was added 10 gm [0.0199 moles] of p-nitrobenzyl-7-phenoxyacetamido-2,2-dimethylpenam-3-carboxylate-1-oxide and 4.12 gm [0.022 moles] of N-chlorophthalimide and refluxed for 120 min. After cooling and stirring for 30 min. at 10° C., the suspension was filtered and the filtrate cooled to −10° C. To the cooled suspension was added 1.24 gm [0.0199 moles] of dimethyl sulfide and 10.36 gm [0.0397 moles] of stannic chloride in 10 ml toluene and the slurry stirred for 16 hrs. at 18° C. and filtered. The complex was washed with pentane and added to methanol at 0° C. and stirred for 4 hrs. at 0° C. The product was filtered, washed with methanol and dried to give 6.5 gm [65%] of title product.

EXAMPLE 28

Preparation of
p-Nitrobenzyl-7-Phenoxyacetamido-3-exomethylene-cepham-4-carboxylate-1-oxide.

8 gm [0.0587 moles] of anhydrous dicalcium hydrogen phosphate in 600 ml toluene was binary distilled to remove moisture. After cooling the suspension to 30° C. was added 10 gm [0.0206 moles] of p-nitrobenzyl-7-phenylacetamido-2-dimethylpenam-3-carboxylate-1-oxide and 4.12 gm [0.022 moles] of N-chlorophthalimide and refluxed for 120 min. After cooling and stirring for 30 min. at 10° C., the suspension was filtered and the filtrate cooled to −10° C. To the cooled suspension was added 1.51 gm [0.0199 moles] of carbon disulfide and 10.36 gm [0.0397 moles] of stannic chloride in 10 ml of toluene and the slurry stirred for 16 hrs. at 18° C. and filtered. The complex was washed with pentane and added to methanol at 0° C. and stirred for 4 hrs. at 0° C. The product was filtered, washed with methanol and dried to give 6.45 gm [64.5%] of title product.

EXAMPLE 29

Preparation of
p-Nitrobenzyl-7-Phenoxyacetamido-3-exomethylene-cepham-4-carboxylate-1-oxide.

4 gm [0.0302 moles] of anhydrous diammonium phosphate in 300 ml toluene was binary distilled to remove moisture. After cooling the suspension to 30° C., add 5 gm [9.98 m moles] of p-nitrobenzyl-7-phenoxyacetamido-2,2-dimethylpenam-3-carboxylate-1-oxide and 1.99 gm [0.0109 moles] of N-chlorophthalimide and reflux for 120 min. After cooling and stirring for 30 min. at 10° C., the suspension was filtered and the filtrate cooled to −10° C. To the cooled suspension was added 0.62 gm [9.98 m moles] of dimethyl sulfide and 5.2 gm [0.0199 moles] of stannic chloride in 5 ml toluene and the slurry stirred for 16 hrs. at 18° C. and filtered. The complex was washed with pentane and added to methanol at 0° C. and stirred for 4 hrs. at 0° C. The product was filtered, washed with methanol and dried to give 5.0 gm [50%] of title product.

EXAMPLE 30

Preparation of
p-Nitrobenzyl-7-Phenoxyacetamido-3-exomethylene-cepham-4-carboxylate-1-oxide.

4 gm [0.0302 moles] of diammonium phosphate in 300 ml toluene was binary distilled to remove moisture. After cooling the suspension to 30° C., add 5 gm [9.98 moles] of p-nitrobenzyl-7-phenoxyacetamido-2,2-dimethylpenam-3-carboxylate-1-oxide and 1.99 gm [0.0109 moles] of N-chlorophthalimide and reflux for 120 min. After cooling and stirring for 30 min. at 10° C., the suspension was filtered and the filtrate cooled to −10° C. To the cooled suspension was added 0.758 gm [9.98 moles] of carbon disulfide and 5.2 gm [0.0199 moles] of stannic chloride in 5 ml toluene and the slurry stirred for 16 hrs. at +18° C. and filtered. The complex was washed with pentane and added to methanol at 0° C. and stirred for 4 hrs. at 0° C. The product was filtered, washed with methanol and dried to give 4.52 gm [45.2%] of title product.

We claim:

1. A process for the manufacture of 3-exomethylene cepham sulfoxide ester of the formula

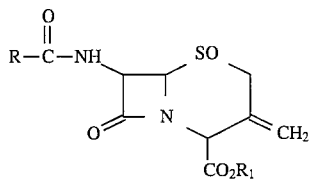

wherein R is benzyloxy and $R_1$ is para nitrobenzyl, which comprises reacting a chlorosulfinylazetidinone compound of the formula

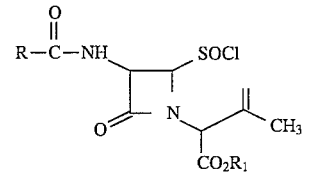

with a Lewis Acid type Friedel-Crafts catalyst selected from covalent chlorides of Sn(IV), Ti(IV) or Zr(IV) in an amount of 2–3 moles per mole of said chlorosulfinylazetidinone and a sulfur compound selected from dimethylsulfide, phenyl sulfide, penta methylene sulfide, dimethyl sulfoxide, dibenzyl sulfide, or carbon disulfide in an amount of 1 to 1.5 moles per mole of chlorosulfinylazetidinone compound in an inert solvent at a temperature of between −15° C. to 45° C. under anhydrous conditions.

2. A process for the manufacture of 3-exomethylene cepham sulfoxide ester of the formula

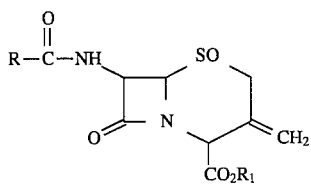

wherein R is hydrogen, $C_1$–$C_3$ alkyl, halomethyl, phenyl, cyanomethyl, phenoxy, benzyloxy, or substituted benzyl with a substituent group selected from halo, alkyl, alkoxy, protected hydroxy, nitro, cyano or trifluoromethyl; or R is a group of the formula $R_3$—$(0)_n$—$CH_2$, wherein $R_3$ is phenyl or substituted phenyl with a substituent selected from halo, alkyl, alkoxy, protected hydroxy, nitro, cyano, or 1,4-cyclohexadienyl, and n is 0 or 1; and $R_1$ is a carboxylic acid protecting group selected from the group consisting of $C_1$–$C_4$ alkyl, 2,2,2,-trihalo alkyl, benzyl, para nitrobenzyl, phenacyl, halo substituted phenacyl and benzhydryl which comprises reacting a chlorosulfinylazetidinone of the formula

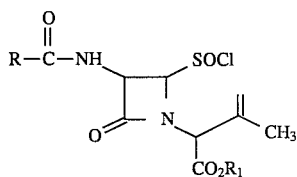

with a Lewis Acid type Friedel-Crafts catalyst selected from covalent chlorides of Al, Sn(IV), Fe(III), Ti(IV) or Zr(IV) in an amount of 2–3 moles per mole of said chlorosulfinylazetidinone and a sulfur compound selected from dimethylsulfide, dipentyl sulfide, diethyl sulfide, cyclopentyl sulfide, phenyl sulfide, penta methylene sulfide, cyclohexyl sulfide, tetra hydro thiophene, penta methylene thioether diphenyl sulfide, dimethyl sulfoxide, dibenzyl sulfide, or carbon disulfide or mixtures thereof in an amount of 1 to 1.5 moles per mole of chlorosulfinylazetidinone compound in an inert solvent at a temperature of between –15° C. to 45° C. under anhydrous conditions.

3. A process for the manufacture of 3-exomethylene cepham sulfoxide ester of the formula

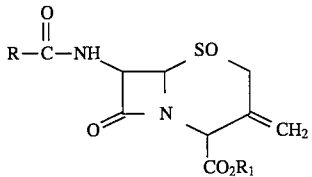

wherein R is hydrogen, $C_1$–$C_3$ alkyl, halomethyl, phenyl, cyanomethyl, phenoxy, benzyloxy, or substituted benzyl with a substituent group selected from halo, alkyl, alkoxy, protected hydroxy, nitro, cyano or trifluoromethyl; or R is a group of the formula $R_2$—0 wherein $R_2$ is t-butyl, 2,2,2-trichloro ethyl or benzyl; or R is a group of the formula $R_3$—$(0)_n$—$CH_2$, wherein $R_3$ is phenyl or substituted phenyl with a substituent selected from halo, alkyl, alkoxy, protected hydroxy, nitro, cyano, or 1,4-cyclohexadienyl, and n is 0 or 1; or R is a substituted arylalkyl group of formula

where $R_4$ has the same meaning as $R_3$ defined above and W is a protected hydroxy or protected amino group; and $R_1$ is a carboxylic acid protecting group selected from the group consisting of $C_1$–$C_4$ alkyl, 2,2,2-trihalo alkyl, benzyl, para nitrobenzyl, phenacyl, halo substituted phenacyl and benzhydryl which comprises reacting a chlorosulfinylazetidinone of the formula

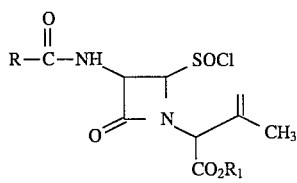

with a Lewis Acid type Friedel-Crafts catalyst selected from covalent chlorides of Al, Sn(IV), Fe(III), Ti(IV) or Zr(IV) in an amount of 2–3 moles per mole of said chlorosulfinylazetidinone and a sulfur compound selected from dimethylsulfide, dipentyl sulfide, diethyl sulfide, cyclopentyl sulfide, phenyl sulfide, penta methylene sulfide, cyclohexyl sulfide, tetra hydro thiophene, penta methylene thioether diphenyl sulfide, dimethyl sulfoxide, dibenzyl sulfide, or carbon disulfide or mixtures thereof in an amount of 1 to 1.5 moles per mole of chlorosulfinylazetidinone compound in an inert solvent at a temperature of between –15° C. to 45° C. under anhydrous conditions.

4. A process for the manufacture of 3-exomethylene cepham sulfoxide ester of the formula

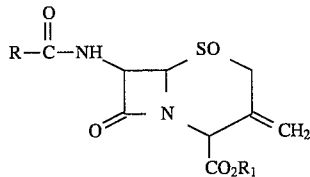

wherein R is hydrogen, $C_1$–$C_3$ alkyl, halomethyl, phenyl, cyanomethyl, phenoxy, benzyloxy or substituted benzyl with a substituent group selected from halo, alkyl, alkoxy, protected hydroxy, nitro, cyano or trifluoromethyl; or R is a group of the formula $R_2$—O— wherein $R_2$ is t-butyl, 2,2,2-trichloro ethyl or benzyl; or R is a group of the formula $R_3$—$(0)_n$—$CH_2$, wherein $R_3$ is phenyl or substituted phenyl with a substituent group selected from halo, alkyl, alkoxy, protected hydroxy, nitro, cyano, or 1,4-cyclohexadienyl, and n is O or 1; or R is a substituted arylalkyl group of formula

where $R_4$ has the same meaning as $R_3$ defined above and W is a protected hydroxy or protected amino group; and $R_1$ is a carboxylic acid protecting group selected from the group consisting of $C_1$–$C_4$ alkyl, 2,2,2-trihalo alkyl, benzyl, para nitrobenzyl, phenacyl, halo substituted phenacyl or benzhydryl which comprises reacting a chlorosulfinylazetidinone compound of the formula

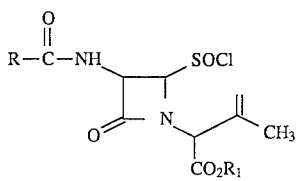

to which a sulfur compound selected from dimethylsulfide, dipentyl sulfide, diethyl sulfide, cyclopentyl sulfide, cyclohexyl sulfide, tetra hydro thiophene, phenyl sulfide, penta methylene sulfide, penta methylene thioether diphenyl sulfide, dimethyl sulfoxide, dibenzyl sulfide, or carbon disulfide or mixtures thereof in an amount of 1 to 1.5 moles per mole of chlorosulfinylazetidinone compound has been added with a Lewis Acid type Friedel-Crafts catalyst selected from covalent chlorides of Al, Sn(IV), Fe (III), Ti(IV) and Zr(IV) in an amount of 2 to 3 moles per mole of chlorosulfinylazetidinone compound in an inert solvent at a temperature of between −15° C. to 45° C. under anhydrous conditions.

5. A process for the manufacture of 3-exomethylene cepham sulfoxide ester of the formula

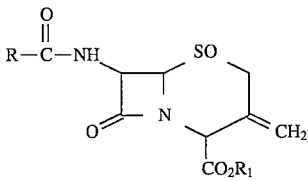

wherein R is hydrogen, $C_1$–$C_3$ alkyl, halomethyl, phenyl, cyanomethyl, phenoxy, benzyloxy or substituted benzyl with a substituent group selected from halo, alkyl, alkoxy, protected hydroxy, nitro, cyano or trifluoromethyl; or R is a group of the formula $R_2$—O— wherein $R_2$ is t-butyl, 2,2, 2-trichloro ethyl, benzyl or substituted benzyl; or R is a group of the formula $R_3$—(O)$_n$—$CH_2$, wherein $R_3$ is phenyl or substituted phenyl with a substituent selected from halo, alkyl, alkoxy, protected hydroxy, nitro, cyano, or 1,4-cyclohexadienyl, and n is 0 or 1; or R is a substituted arylalkyl group of formula

where $R_4$ has the same meaning as $R_3$ defined above and W is a protected hydroxy or protected amino group; and $R_1$ is a carboxylic acid protecting group selected from the group consisting of $C_1$–$C_4$ alkyl, 2,2,2-trihalo alkyl, benzyl, para nitrobenzyl, phenacyl, halo substituted phenacyl or benzhydryl which comprises reacting a chlorosulfinylazetidinone compound of the formula

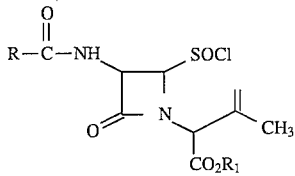

with a catalyst complex of a Lewis Acid type Friedel-Crafts catalyst and a sulfur compound, said Lewis Acid type Friedel-Crafts catalyst selected from covalent chlorides of Al, Sn(IV), Fe (III), Ti(IV) and Zr(IV) in an amount of 2 to 3 moles per mole of chlorosulfinylazetidinone compound and said sulfur compound selected from dimethylsulfide, dipentyl sulfide, diethyl sulfide, cyclopentyl sulfide, cyclohexyl sulfide, tetra hydro thiophene, phenylsulfide, pentamethylene sulfide, penta methylene thioether diphenyl sulfide, dimethyl sulfoxide, dibenzyl sulfide, or carbon disulfide or mixtures thereof in an amount of 1 to 1.5 moles per mole of chlorosulfinylazetidinone compound, in an inert solvent at a temperature of between −15° C. to 45° C. under anhydrous conditions.

6. The process as claimed in claim 1 wherein the inert organic solvent is toluene, benzene or xylene.

7. The process as claimed in claim 2 wherein the inert organic solvent is toluene, benzene or xylene.

8. The process as claimed in claim 3 wherein the inert organic solvent is toluene, benzene or xylene.

9. The process as claimed in claim 4 wherein the inert organic solvent is toluene, benzene or xylene.

10. The process as claimed in claim 5 wherein the inert organic solvent is toluene, benzene or xylene.

11. The process as claimed in claim 1 wherein the process is carried out for 16 to 24 hours.

12. The process as claimed in claim 2 wherein the process is carried out for 16 to 24 hours.

13. The process as claimed in claim 3 wherein the process is carried out for 16 to 24 hours.

14. The process as claimed in claim 4 wherein the process is carried out for 16 to 24 hours.

15. The process as claimed in claim 5 wherein the process is carried out for 16 to 24 hours.

\* \* \* \* \*